United States Patent [19]

Higson et al.

[11] Patent Number: 4,976,259
[45] Date of Patent: Dec. 11, 1990

[54] ULTRASONIC NEBULIZER

[75] Inventors: James R. Higson, Santa Barbara; David A. D'Alfonso, Goleta; Robert R. Walls, Santa Barbara, all of Calif.

[73] Assignee: Mountain Medical Equipment, Inc., Denver, Colo.

[21] Appl. No.: 266,823

[22] Filed: Nov. 2, 1988

Related U.S. Application Data

[63] Continuation-in-part of Ser. No. 944,203, Dec. 22, 1986, abandoned.

[51] Int. Cl.⁵ .............................................. A61M 11/00
[52] U.S. Cl. ............................ 128/200.18; 128/200.16; 128/200.14; 238/107.1
[58] Field of Search ...................... 128/200.14, 200.16, 128/200.18; 239/102.1, 102.2

[56] References Cited

U.S. PATENT DOCUMENTS

| | | | |
|---|---|---|---|
| 3,433,461 | 3/1969 | Scarpa | 259/1 |
| 3,774,602 | 11/1973 | Edwards | 128/194 |
| 3,828,773 | 8/1974 | Buch et al. | 239/102.2 |
| 3,861,386 | 1/1975 | Harris et al. | 128/194 |
| 3,866,831 | 2/1975 | Denton | 239/102.2 |
| 3,989,042 | 11/1976 | Mitsui et al. | 128/194 |
| 4,001,650 | 1/1977 | Romain | 317/41 |
| 4,094,317 | 6/1978 | Wasnich | 128/194 |
| 4,109,863 | 8/1978 | Olson et al. | 239/102 |
| 4,113,809 | 9/1978 | Abair et al. | 261/81 |
| 4,646,967 | 3/1987 | Geithman | 239/102.2 |

Primary Examiner—Randall L. Green
Assistant Examiner—K. M. Reichle
Attorney, Agent, or Firm—John E. Reilly

[57] ABSTRACT

An ultrasonic nebulizer is of the type having a piezoelectric transducer communicating with a fluid reservoir and is characterized by having a protective cover of a predetermined wavelength which is superimposed on the transducer, an elastomeric boot in surrounding relation to the cover to prevent fluid loss from the interface between the cover and transducer, and an oil coupling medium is disposed in the interface for coupling the ultrasonic energy from the transducer to the cover.

10 Claims, 6 Drawing Sheets

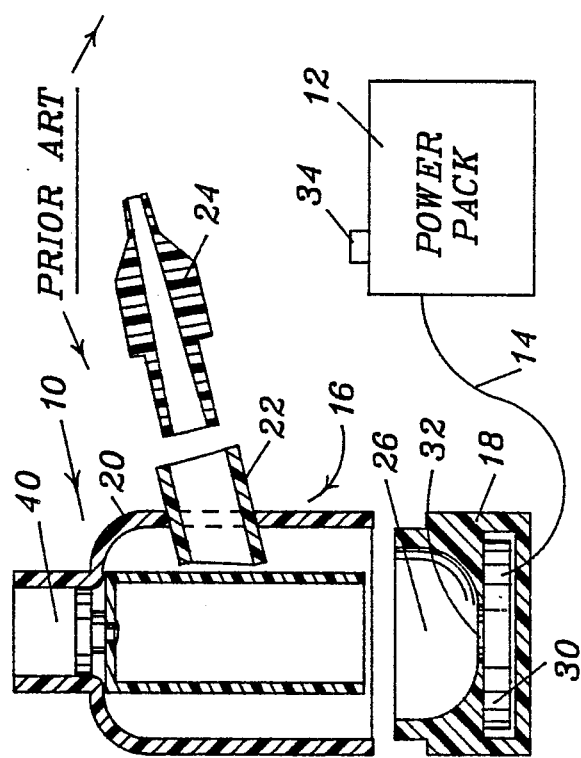
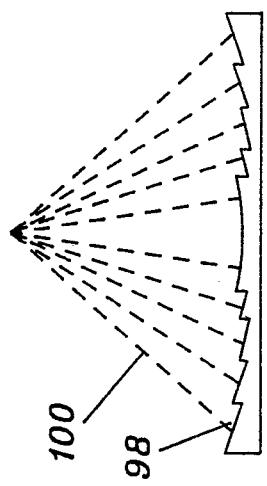
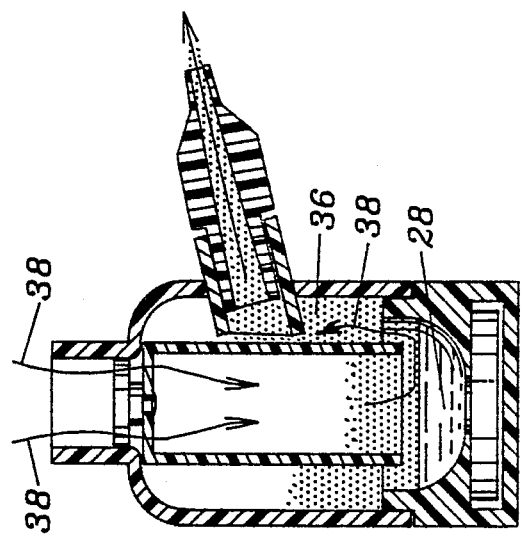

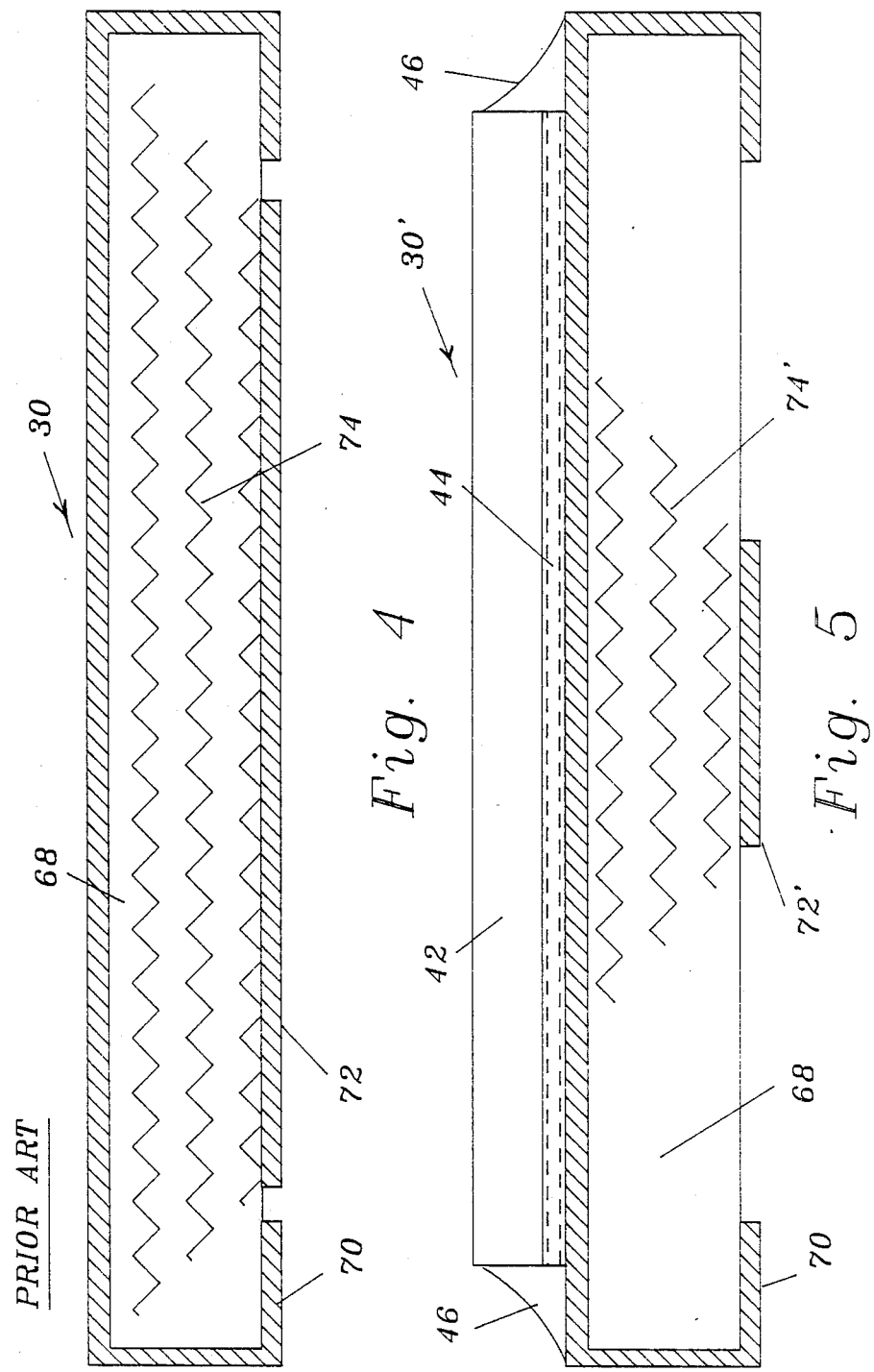

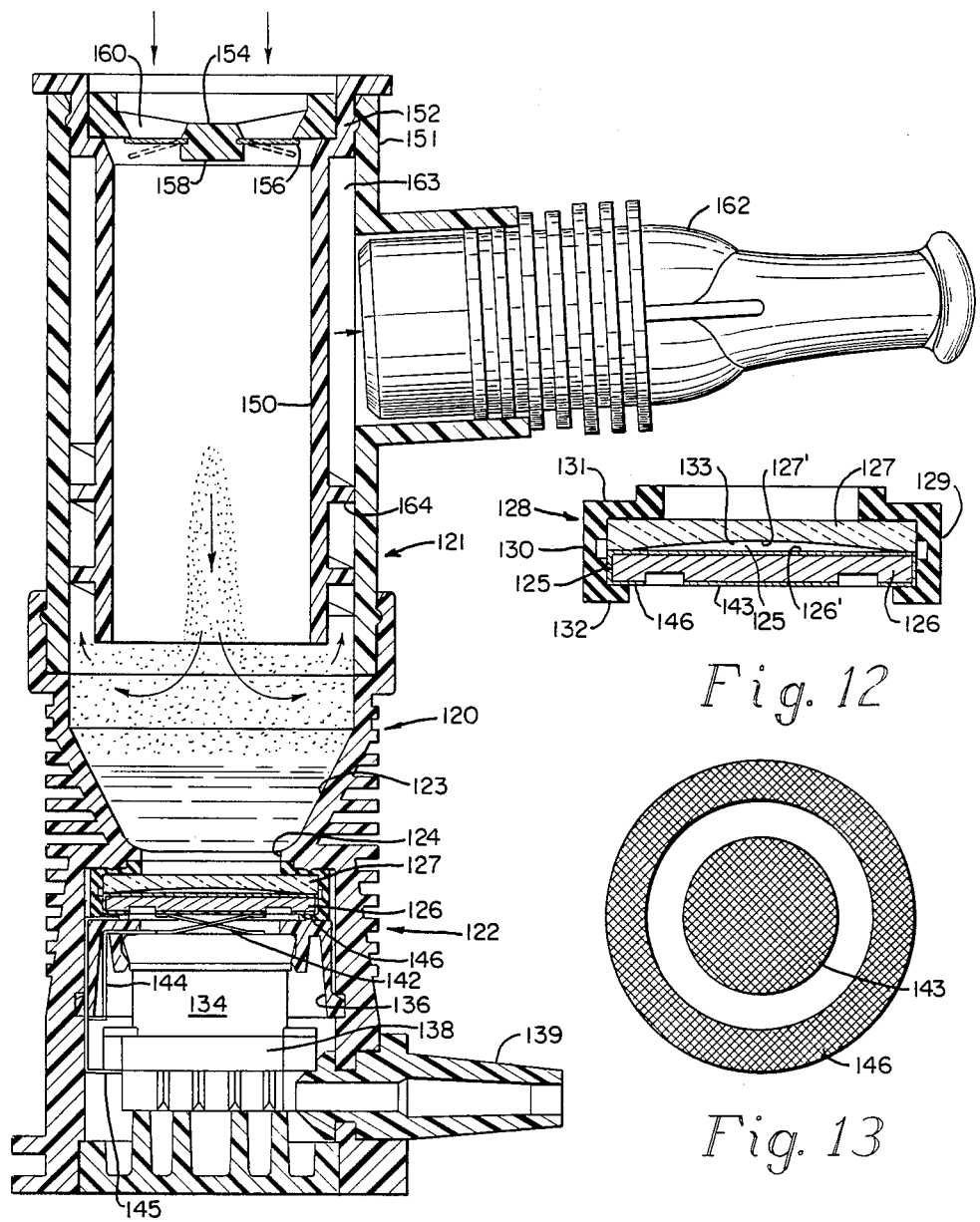
Fig. 11
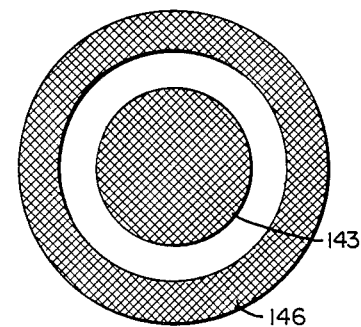
Fig. 12
Fig. 13

ULTRASONIC NEBULIZER

CROSS REFERENCE TO RELATED APPLICATIONS

This is a continuation-in-part application of Ser. No. 944,203, filed Dec. 22, 1986, now abandoned by James R. Higson et al, and assigned to the assignee of the present invention. This invention relates to medical devices for the inhalation of medication and, more particularly, to a novel and improved nebulizer which is specifically adapted for use in the inhalation of medication but having useful application on other devices employing a piezoelectric crystal for ultrasonic stimulation and excitation such as emulsifiers, cleaners and the like.

BACKGROUND AND FIELD OF THE INVENTION

Pulmonary drug delivery systems, commonly referred to medically as nebulizers, come in various forms. These, in turn can be broken down into various sub-groups. For example, the atomizer type of device uses the venturi principle of air passing across a pipe or orifice to draw liquid medication from a storage receptical and atomize it into small particles. Such devices can be operated by squeezing a bulb or with a pressurized container.

When ultrasonic energy of the right frequency and power is applied to a liquid, a very fine particle mist is released from the surface. At the frequency required to convert liquids, such as, water to a mist, the ultrasonic energy can be produced by electrically exciting a piezoelectric-material, such as, lead zirconate titonate, and mechanically coupling that material to the liquid. Of the total energy which enters a system of this type, some is converted to heat in the piezoelectric material, some may be converted to heat in the liquid, and the remainder is consumed at the liquid surface in the process of breaking away particles to form the mist.

In a medical application, this process is called nebulization and is used to convert medication to a mist for inhalation in the treatment of respiratory disease. In order to do this most effectively, the medication should be nebulized into particles or droplets of a particular size range and, as a general rule, the smaller the particles the better the penetration of the particles into the lungs and the bronchial passageways.

Earlier versions of ultrasonic nebulizers were intended for use primarily in the home or medical facility environment. However, miniaturization and the availability of small, highly efficient, rechargeable battery packs make it highly desirable to provide portable ultrasonic nebulizers which can be hand-carried and used as required in the treatment of respiratory disease.

In the past, ultrasonic nebulizers which have employed a piezoelectric material have encountered numerous problems, among which is the tendency of the material to rapidly degrade owing to the generation of heat, cavitation of the liquid caused by the high acoustic energy level, and chemical attack of the surface by medications and cleaning agents. Each time that acoustic energy crosses from one material to another, some is passed and some is reflected. Any material positioned between the transducer and the liquid for protecting the surface should possess high energy transmission efficiency and low energy reflection back to the transducer. It has been found that this condition can be created by providing a thin coating or plating of approximately 1/100 W, such as, teflon, polyimide or gold, or providing a cover having a thickness of W/2 or a multiple thereof, such as, W, 3W/2, 2W attached to the transducer surface where $W_\infty$ is the wavelength of the excitation signal. Glass is a preferred material for such a cover because it presents an easily cleaned and durable surface to the liquid and can tolerate high temperatures. Nevertheless, a coupling agent is required to bridge the air gap between the two surfaces. In U.S. Pat. No. 4,109,863 to Olson et al, it was proposed to employ adhesives for this purpose. However, high temperatures tend to weaken the bond of the adhesive and cause poor acoustic coupling and increased reflected energy. Olson et al proposed to solve the problem of high temperatures at the transducer surface by circulating a cooling water over the transducer and glass, but this method is not feasible for a portable handheld device and has the additional undesirable effect of acoustically damping the back side of the transducer and thus reducing the efficiency of the nebulizer system.

We have found it desirable to employ oil of the correct viscosity and temperature capability as a coupling agent. The oil tends to migrate toward the high energy density center of the transducer/glass interface and occurs even after high temperatures have forced some of the oil to the periphery. In order to overcome any tendency of the oil film to be too thin, causing reduced nebulization, the gap between the protective cover and the transducer surface must be so shaped as to provide an optimum oil film thickness thereacross which will avoid regularly generated reflections. Also it is important to contain the oil so that gravity and capillary forces do not carry it away from the gap during periods of inactivity. Accordingly it is important that the oil be confined or sealed in such a way as to assure that it will migrate towards the center of the gap when energy is applied. Moreover, another problem associated with the use of oil as a coupling agent is the presence of entrapped gas which, when released during operation, may displace the oil and uncouple the glass cover. It is therefore desirable to minimize the amount of entrapped gas present in the oil in the process of assembling the elements of the nebulizer and to make provision for accumulation of any entrapped gas which may escape from the transducer surface during its life.

Among various other prior art techniques, U.S. Pat. No. 3,433,461 to Scarpa employs a piezoelectric crystal bonded to a support layer. Both the crystal and the support layer were chosen to be one-half wavelength in thickness and bonded together with an adhesive to form a composite structure one wavelength in thickness. This structure is supported around its periphery and contains a thin web between the vibrating center and supported periphery to prevent support structure loading which is counter productive to efficient high energy vibration. Other patents of interest are U.S. Pat. No. 4,094,317 to Wasnich and U.S. Pat. No. 3,861,386 to Harris where an acoustic wave form is shaped to perform ultrasonic nebulization of the liquid and to isolate the liquid from the piezoelectric crystal and prevent dry operation of the device.

SUMMARY OF THE INVENTION

It is therefore an object of the present invention to provide for a novel and improved ultrasonic nebulizer which is capable of efficient acoustical coupling of energy from a piezoelectric crystal into the medication being nebulized without significant attenuation and wherein the crystal itself is protected from undesired early destruction.

Another object of the present invention is to provide in an ultrasonic nebulizer for a novel and approved piezoelectric transducer and wherein the means for acoustically coupling the ultrasonic energy from the piezoelectric element to a face plate is a liquid; and further wherein the gap formed between the face plate and piezoelectric element is so formed that the energy transfer is maximized and heating minimized so as to avoid the necessity for external means of cooling.

A further object of the present invention is to provide in an ultrasonic nebulizer for a novel and improved method and means for mounting a piezoelectric crystal and protective cover and face plate which will maintain an optimum gap between the elements notwithstanding pressure increases created by thermal expansion of the coupling fluid; and further wherein the mounting means will act as a reservoir for the coupling fluid and retain any entrapped gases therein so as to prevent decay of the coupling efficiency otherwise resulting from gas build up.

It is an additional object of the present invention to provide for a method of assembly of a piezoelectric crystal in an ultrasonic nebulizer to minimize the amount of entrapped gases in a coupling fluid between the crystal and face plate and to effectively seal the crystal and the face plate along with the coupling fluid for most efficient energy transfer between the crystal and the face plate.

It is still an additional object of the present invention to provide for a novel and improved nebulizer which will maximize the isolation and removal of optimum size particles for inhalation by the user as well as to more effectively collect and renebulize larger particles in such a way as to minimize clogging or impaction of the particles.

In accordance with the present invention, the foregoing objectives have been attained in an assembly having a cavity therein for holding a liquid medication to be nebulized by a piezoelectric crystal disposed in communication with the cavity and separated from medication contained in the cavity by a thin cover of a material having characteristics for allowing it to match acoustical impedances without significant attenuation, such as, those possessed by glass, the crystal being disposed adjacent to the cover; a thin film of an energy-coupling fluid interposed between the cover and the surface of the crystal; and, sealing means for the cover and the surface of the crystal for preventing loss of fluid from between the cover and the surface of the crystal.

In one embodiment, the cavity has a hole in the bottom thereof communicating with the surface of the crystal; and, the cover comprises a sheet of glass, or the like, disposed over the surface of the crystal.

In a second embodiment, the cavity has a hole in the bottom thereof communicating with the surface of the crystal; and, the cover comprises the bottom of a unitary bowl insert of a glass-like material inserted into the cavity. In a third embodiment, the bowl unit is of unitary construction and the cover comprises the bottom of the cavity which is formed therein.

In a preferred apparatus for the ultrasonic nebulization of fluids wherein a piezoelectric transducer is disposed in communication with a reservoir for nebulizing liquid medication in the reservoir, the improvement comprises a protective cover member of a predetermined wavelength superimposed on the transducer, the cover member and transducer having generally planar confronting surfaces and a common interface therebetween, annular sealing means in outer surrounding relation to the cover member to prevent the loss of fluid from the interface, and oil coupling means in the interface for coupling the ultrasonic energy from the transducer to the cover member. Most desirably the transducer is a piezoelectric crystal having a top electrode extending down the sides and wrapping around the bottom edge and a bottom disc electrode of substantially smaller diameter than the diameter of the piezoelectric crystal whereby the electrical contact to the bottom of the piezoelectric crystal thereof is adjacent to the center thereof.

DESCRIPTION OF THE DRAWINGS

FIG. 1 is a partially exploded, simplified, cutaway drawing of a prior art ultrasonic nebulizer;

FIG. 2 is a drawing of the prior art nebulizer of FIG. 1 shown assembled and showing its manner of operation;

FIG. 4 is a simplified cutaway drawing through a piezoelectric crystal as employed in prior art ultrasonic nebulizers showing the manner of vibrational propagation therethrough;

FIG. 5 is a simplified cutaway drawing through a piezoelectric crystal as employed in the ultrasonic nebulizer of the present invention with its protective covering and showing the manner of vibrational propagation therethrough;

FIG. 8 is a simplified cutaway drawing through a prior art vibrational surface specially shaped to direct the energy waves toward the center thereof;

FIG. 11 is a sectional view of a preferred form of portable nebulizer unit in accordance with the present invention;

FIG. 12 is a detailed view in section of the piezoelectric transducer assembly; and FIG. 13 is a bottom view of the preferred form of crystal employed in accordance with the present invention.

DETAILED DESCRIPTION OF THE PREFERRED EMBODIMENT

Figure 9:
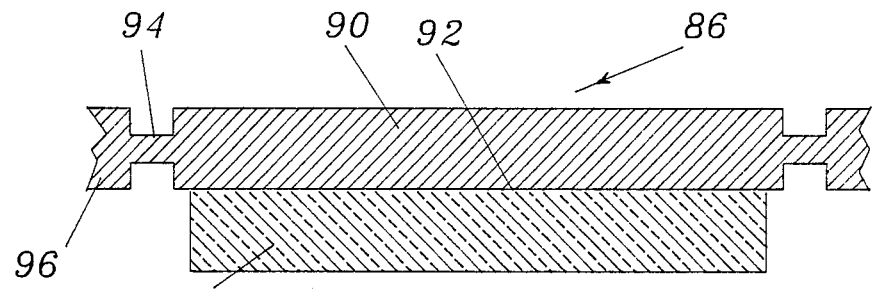
FIG. 9 is a simplified cutaway drawing through a prior art composite structure for a piezoelectric crystal wherein the crystal is adhesively attached to a vibrating support structure and the virbating portion is decoupled from the actual support area.

As a setting for the present invention, prior art nebulizers, such as, that generally indicated at 10 in FIG. 1 in exploded view, comprise a power pack 12 containing batteries, not shown, if it is a portable unit, or are adapted to be plugged into a wall outlet in the case of non-portable units. The power pack 12 is connected by power cable 14 to the nebulizing unit 16. The nebulizing unit 16, in turn, comprises a bowl portion 18 over which a cover 20 is adapted to be positioned. The cover 20 has a mouthpiece mounting tube 22 through the sidewalls thereof into which mouthpiece 24 can be press fit. For ease of manufacture and assembly, the bowl portion 18, cover 20, tube 22 and mouthpiece 24 are usually cylindrical in cross section. The same components are also typically made of high impact plastic for light weight, ease of cleaning, and non-contamination. The bowl portion 18 contains a bowl-shaped cavity 26 in the top thereof into which the liquid medication 28 (see FIG. 2) is poured. A piezoelectric crystal 30 is positioned under the cavity 26 and the bottom of the cavity 26 has a circular hole 32 therein communicating with the top of the piezoelectric crystal 30. To activate the unit, the button 34 on the top of the power pack 12 is depressed, causing the piezoelectric crystal 30 to have power applied thereto. That, in turn, causes the crystal 30 to vibrate at ultrasonic frequency and nebulize a portion of the liquid medication disposed within the hole 32 and on top of the surface of the piezoelectric crystal 30. The atomized droplets 36 produced are inhaled through the mouthpiece 24 in combination with air, indicated by the arrows 38, which is drawn in through the entry pipe 40 in the top of the cover 20 provided for that purpose.

Such prior art devices made and operating according to the foregoing description work adequately for their intended purpose with a major shortcoming that the piezoelectric crystal is rapidly destroyed in the process. This, of course, requires frequent and costly repair or replacement of the bowl portion 18. One problem with using a bare crystal is that the plated electrode thereof is attacked by some of the cleaning solutions (e.g., vinegar). Another problem arises because of the wide difference between the acoustical impedances of a water based liquid (i.e., the medication to be nebulized) and air. If the acoustical impedances are properly matched, then the acoustical energy is radiated; if not, a majority of the energy is reflected back into the crystal. When the energy is reflected back, it is in a very small region and produces high localized temperatures. These high temperatures tend to cause the crystal material, along with its plated electrode, to rapidly degrade. When there is medicine present, a good acoustical impedance match exists and there is good nebulization. When the medicine is not present or exists in only a thin layer, a poor acoustical impedance match exists, causing very destructive conditions for the crystal. When the bare crystal fails due to the acoustical impedance mismatch, the high energy densities locate in the interface between the plated electrode and the piezo crystal itself. This develops thermal gradients which, in turn, cause the plating to develop pin holes therethrough. Once the pin holes appear, the plating quickly degrades as the medicine seeps in. Additionally, cavitation effects accelerate the destruction once the holes appear.

Attempts at coating the piezoelectric crystal have met with little or no success to date. Either the ultrasonic vibration of the crystal is not coupled into the covering, or poorly coupled, such that nebulization is inefficient or nonexistent; or, the coating is simply destroyed in the same manner, followed shortly thereafter by the crystal itself. For example, with a coating, such as, Teflon or a high temperature polyimide as previously employed in the art, the same impedance problem is encountered; except, it is complicated by the coating having its own characteristic acoustic impedance as well. Now, the energy is concentrated in the interface between the electrode and the coating. Subsequently, the coating sees the high energy densities and associated thermal gradients. Failure is quite similar to the bare crystal. Small bubbles first begin to appear in the center of the assembly, i.e., the most active portion. Once a bubble appears, the assembly quickly degrades in the manner described above.

In the prior art structure of FIG. 9, the piezoelectric crystal 88 is bonded to a support layer 90 which actually contacts the liquid. Both the crystal 88 and the support layer 90 were chosen to be one-half wavelength in thickness and then bonded together with an adhesive 92 to form a composite structure 86 one wavelength in thickness. The composite structure 86 is supported about its periphery and contains a thin web 94 between the vibrating center portion and the supported periphery 96 to prevent support structure loading thereof which is counterproductive to efficient high energy vibration.

As depicted in FIG. 8, a vibrating surface is shown on which the liquid to be nebulized is in contact in order to focus the energy waves towards the center of the liquid in a concentrated energy area. Thus, for example, the vibrating surface 98 in FIG. 8 is in the form of a Fresnel lens, which aims or directs the vibrational energy, indicated by the dotted lines 100, towards a plane passing through the center.

Figure 10:
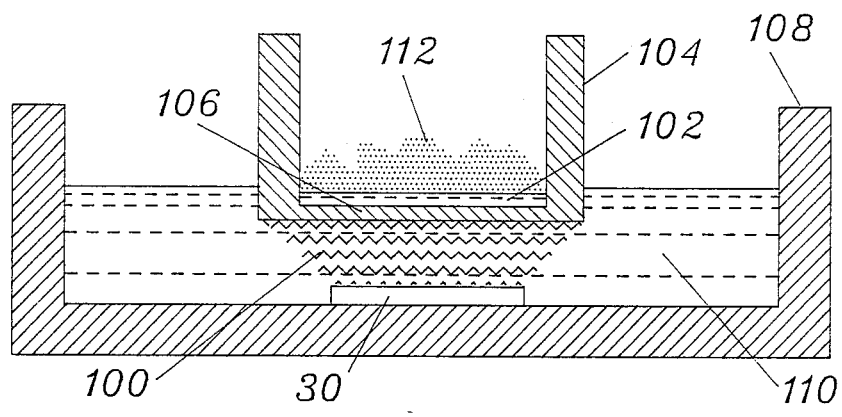
FIG. 10 is a simplified cutaway through a prior art structure wherein the liquid to be nebulized is contained in a separate container.

A second technique is shown in simplified form in FIG. 10 and comprises placing the liquid to be nebulized 102 in a small container 104 having a thin, vibratable bottom surface 106 and placing the small container 104 in a large container 108 filled with liquid 110 (such as water) and having the piezoelectric crystal 30 at the bottom thereof. In this manner, the crystal 30 is always liquid-covered. When the crystal 30 is vibrated, the energy waves travel through the liquid 110 in the large container 108 and strike the bottom surface 106 of the small container 104, causing it to vibrate an amount sufficient to nebulize the liquid 102 and cause the droplets 112.

Figure 3:
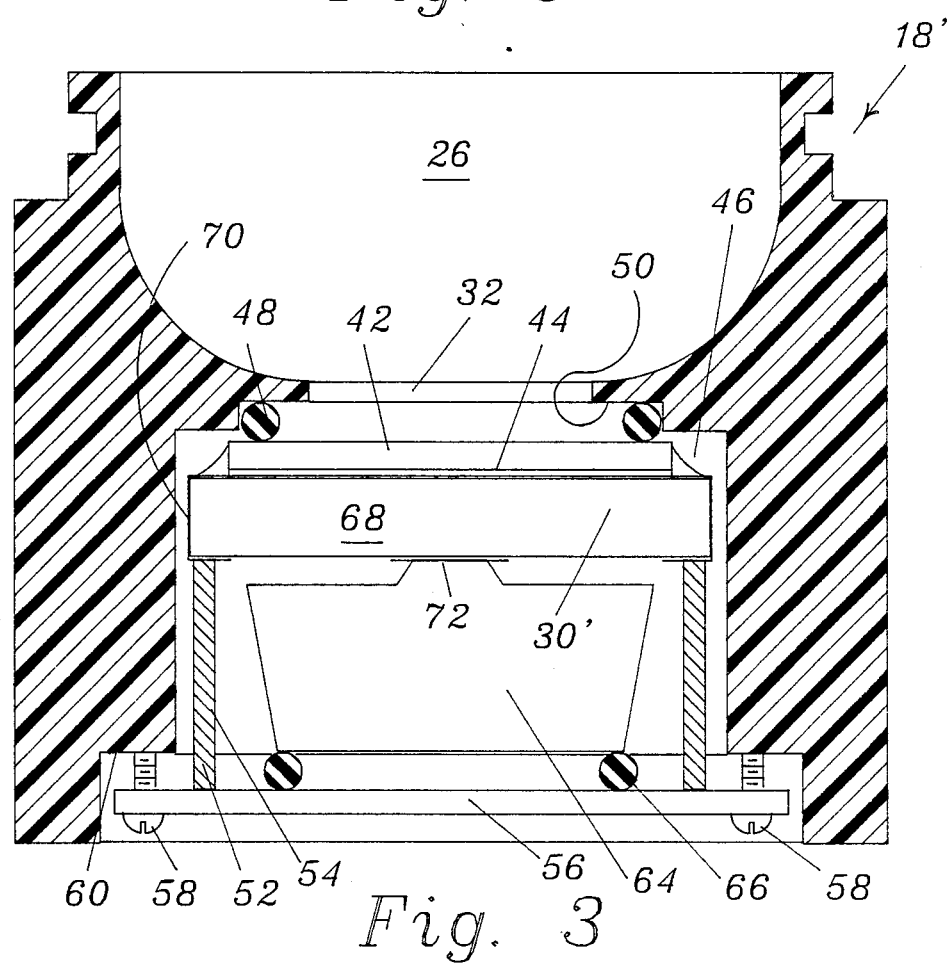
FIG. 3 is an enlarged, detailed, cutaway drawing of the bowl portion of a nebulizer according to the present invention in a first embodiment thereof.

The improved bowl portion of an ultrasonic nebulizer similar to the prior art nebulizer of FIGS. 1 and 2 and modified according to the present invention is shown in detail in FIG. 3 and labelled therein as 18'. It is designed to be used in conjunction with a power pack 12 and cover 20, as previously described with respect to FIGS. 1 and 2, and in the interest of simplicity and the avoiding of redundancy in the description and drawings, those portions will not be shown or described hereinafter.

The improvement to a piezoelectric crystal constructed assembly of the present invention as used in a nebulizer, for example, includes a protective covering for the piezoelectric crystal and a revised construction of the crystal itself. As best seen in the detailed cutaway view of FIG. 3, the piezoelectric crystal 30' of the present invention in the first embodiment thereof has a protective pyrex glass covering 42 disposed over the surface thereof and under the hole 32 in the bottom of the cavity 26. As an indication of the sizes involved in the apparatus being described, in a tested embodiment of this embodiment which is to be commercially manufactured and sold by the assignee of this application, the piezoelectric crystal 30' is 0.77 inches in diameter and the glass covering 42 is 0.61 inches in diameter. The glass covering 42 is one-half wavelength of the crystal's frequency in thickness, which was found to give preferred coupling to the medication 28 shown in FIG. 2. Since the frequency being employed is about 1.65 MHz, the thickness of the glass covering 42 is approximately 0.064 inches. It should be noted at this point that while the tested example being described here employs a protective pyrex glass covering, other materials known to those skilled in the art could, of course, be employed. For example, certain plastics and ceramic materials would undoubtedly make good substitutes. Likewise, while a circular disc is shown and preferred for ease of manufacture, other shapes could, of course, be used and the term "disc" is not to be construed as a limitation, but rather, a term of convenience only.

Employing a glass covering over the piezoelectric crystal bonded by adhesive would not improve greatly over the prior art approaches mentioned above and would suffer from the same problems. Such approach was initially tried by the applicants herein with the expected results, or lack thereof. Primarily, there is a major loss of acoustic coupling of the ultrasonic energy into the glass cover as the adhesive bond deteriorates. One of the possible solutions to the non-coupling problem which was tried was the use of a thin film of commonly available fluids, such as, water as a coupling fluid between the surface of the crystal 30' and the glass 42. While, initially, these fluids would cause coupling of the energy into the glass cover 42, these common coupling fluids were quickly destroyed in operation, resulting in failure of the unit by loss of acoustic coupling of the energy. Extensive testing finally lead to the discovery of certain fluids which, under influence of the ultrasonic vibration, acted exactly contrary to the other, normally thought of, coupling fluids, which had disintegrated in use; that is, while the other, non-useful fluids had migrated to the edges of the glass 42 and crystal 30' and away from the central active zone of vibrational transfer, the workable coupling fluids discovered by the applicants herein tended to migrate to the center under vibrational stimulation and, thereby, effect maximum energy transfer from the crystal 30' into the glass cover 42. Again, it is worthy of note at this point that while fluids of a particular type and exhibiting particular coupling characteristics are described hereinafter by way of example, those skilled in the art will recognize and appreciate that there are other materials, which could be easily overlooked in the broad classification of "fluids", which could be substituted as the coupling fluid. Where the term "fluid" is used in the descriptions herein and in the claims appended hereto, it is the applicants' intent that it be considered in its broadest sense as including other coupling fluids possessing the necessary qualities and characteristics as set forth in detail hereinafter. As to some of the fluids which were tested and found to be unsuitable, some were quickly destroyed while others were not. When destruction was immediate, i.e., in less than ten uses, no amount of time was enough to recover the ability to effectively pass the ultrasonic energy into the medicine bowl. Such fluids included silicone as well as Teflon-based oils and greases. Other fluids failed because of migration out from under the glass. This resulted in excessively long "warm up" times to produce nebulization, which allowed the fluid to go to the center of activity and for electrical conduction through the film of oil between the brass connector ring and the wrap-around electrode. The "oil" fluids ultimately employed by the applicants as a film between the crystal and its closely adjacent, spaced, protective cover have the property of being "self protecting and self healing"; that is, when destructive conditions appear, the oil film will move out of the most active (and destructive) areas. After the detrimental conditions have left; i.e., there is medicine in the bowl and a good impedance match, the oil "pumps" itself back into the necessary areas to allow good acoustic coupling.

The critical properties of acoustic coupling fluids which are appropriate include—viscosity, viscosity breakdown, temperature stability, acoustic impedance, chemical stability, and molecular composition. These properties will now be addressed individually.

Viscosity: Through empirical analysis, the applicants herein were able to determine the workable limits of viscosity. Bounding the low end is the ability to manufacture the assembly. If the fluid is too thin (under 1 centistoke at 100° C. for oil), it is very difficult to intimately join the crystal and the glass without excessive air entrapping itself (enough to significantly decrease life or couple effectively). On the high end (above 100 centistoke at 100° C. for oil), the fluid still passes the acoustical energy; but, attenuation becomes significant. The higher viscosity fluids tested produced lower output as compared to the fluid viscosities. It is desirable for the fluid to have a viscosity curve which is as flat as possible. This provides uniformity as the temperature of the system changes. The preferred viscosity range is between 4 and 10 centistoke at 100° C. for an oil coupling. In this range, there were no detectable differences in either coupling or life.

Viscosity Breakdown: Because of the high energy densities of the reflected acoustic wave when impedances are mismatched (i.e., air only, no medicine) corresponding high temperatures are found in the interface between the crystal and the glass containing the fluid. To maintain the desired viscosity range and reasonable life, the fluid should not undergo permanent changes in viscosity when exposed to the high temperature and energy densities involved.

Temperature Stability: As previously mentioned, the fluid is subject to very high temperature gradients. Therefore, the fluid needs to have high operating temperature limits as well as a reasonably flat viscosity curve. Temperature requirements are met if the flash point is above 200° C. and there is no viscosity breakdown after repeated thermal cycling.

Acoustic Impedance: The fluid must also have an acoustic impedance which is acceptable to the assembly system at the desired frequency without significant attenuation. Ideal impedance matching between the crystal and cover is difficult to attain; however, through empirical testing, the applicants were able to determine that the window of acceptability was fairly large in a given family of fluids.

Chemical Stability: Some of the fluids tested failed to pass the acoustic energy after a limited number of uses. It is hypothesized that the high energy densities and thermal gradients caused the fluids to change chemical composition. Therefore, the fluid needs to maintain chemical composition when exposed to high temperature and energy densities. Synthetic oils appear to have the ability to take the harsh conditions and maintain their initial properties.

Molecular Composition: Some of the fluids which met the above criteria still failed to pass enough acoustic energy to be effective. The applicants' best guess in this regard is that the molecular composition is such that these fluids' molecular composition outweighed the characteristics of the above properties.

Preferred Fluid: The fluid preferred by applicants, as a group, is synthetic oil based. The preferred embodiment as presently employed by the applicants in the commercial embodiments of the present invention is an 8 centistoke (at 100° C.) Polyalphaolefin base oil.

While the discovery of a workable class of fluids to effect coupling was a major breakthrough in the development of a long-lasting ultrasonic nebulizer, it, in turn, created new problems to be solved in the overall design of the bowl portion 18'. Because of the close spacing employed between the glass cover and the crystal, one of the problem phenomena was capillary action of the fluid during periods of non-use; that is, the fluid simply moved to the outer edges of the glass and was lost due to capillary action. There are also transition periods when the unit is turning on and off. During these times, the assembly is attempting to stabilize to the new conditions that the electrical excitement has produced, i.e., mechanical movement. When initially excited, the assembly attempts to pump fluid into the center of activity to correctly match acoustical impedances. The mechanism of this movement is not fully understood but the applicants hypothesize that a slow moving, travelling wave is created between the crystal surface and the protective glass cover similar to peristaltic pumping. This wave slowly brings in the necessary amount of fluid to complete coupling and better match the acoustic impedance of the crystal to the glass and the medication, i.e., the preferred fluids actually make the assembly self-adjusting for optimum performance. Once the acoutic impedances are matched, the glass cover attains similar vibrational characteristics to the crystal, resulting in a stable standing wave with the fluid at the center of the assembly. When the unit is turned off, the hydrodynamic forces, material forces, and geometry of the crystal and the cover tend to remove the fluid that is contained in the valley sections of the previously formed standing wave. Along with the capillary action previously mentioned, the fluid forced out toward the perimeter of the assembly. The net result was a loss of enough fluid to disable the mechanism pumping the fluid into the center of activity, thus ending efficient acoustic coupling.

Initially, the diameter of the glass cover 42 and crystal 30' were made the same and the two were merely pressed into the groove under the hole 32 originally provided for the crystal alone. To solve the problem, after much testing, the sealing configuration of FIG. 3 was finally developed. As can be seen, the diameter of the protective glass cover 42 was made smaller than the diameter of the crystal 30'. After putting the coupling fluid 44 between the glass cover 42 and the surface of the crystal 30', the circumferencial edge was sealed with an adhesive 46. The preferred adhesive 46 sealing material is a two part epoxy which, when fully cured, provides a hard, rigid, attachment as well as sealing in the coupling fluid. Like the surface of the crystal 30', however, if exposed to the medication 28 at ultrasonic vibrational frequencies, the epoxy adhesive 46 would be quickly destroyed. To eliminate that undesired side effect, a second seal was provided to isolate the edge seal of the epoxy adhesive 46 from the medication 28. That second seal is provided by positioning the edge of the outer periphery of the protective glass 42 and the adhesive 46 outside of the O-ring 48 and which is disposed in a circular groove 50 provided therefor below and surrounding the hole 32. O-ring 48 is of a diameter less than the diameter of the glass cover 42 and greater than the diameter of the hole 32.

The crystal 30', protective glass cover 42 and O-ring 48 are held in position for operation under the bowl-shaped cavity 26 by the same mounting apparatus as in the prior art ultrasonic nebulizers previously discussed broadly under Background of the Invention. In particular, a metal cylindrical contact 52 connected to one wire 54 within power cable 14 is supported against the bottom of the crystal 30' by cylindrical plate 56 as a result of the screws 58 threaded into the bottom 60 of the bowl portion 18'. To provide protection against overheating of the crystal 30', a thermal switch 62, connected to the other wire 64 within power cable 14, is pushed up against the bottom of the crystal 30' by insulating O-ring 66 and plate 56 in a manner common in the prior art.

Turning now to FIGS. 4 and 5 with particularity, the changes to prior art piezoelectric crystals to optimize the particular objectives of the present invention will now be described in detail. As shown in FIG. 4, a piezoelectric crystal 30 as employed in prior art ultrasonic nebulizers, emulsifiers, cleaners, and the like, comprises a circular disc 68 of piezoelectric crystal material. Over the disc 68 two metal electrical contacts 70, 72 are bonded or plated. The upper contact 70 covers the top and sides and extends just around the bottom edge of the disc 68. The bottom contact 72 is a disc that covers the bottom of the disc 68 except for a small circumferencial spacing from the edge of the contact 70 to provide electrical isolation therefrom. Electrical contact is provided totally on the bottom surface with the contacts 70, 72 via the cylindrical contact 52 and thermal switch 64, respectively. The result is a vibrational pattern such as that indicated by the vibrational waves 74 of FIG. 4 which affects the total diameter of the piezoelectric crystal 30. A similar pattern is obtained where the contacts comprise plating of the upper and lower surfaces of the crystal.

To better accomplish the objectives of the present invention, it was hypothesized that if the energy of the crystal 30' could be concentrated in the center where maximum coupling to the glass cover 42 takes place, efficiency would be greatly enhanced due to concentrating the available energy into a smaller area, this smaller area conforming to the mounting scheme used to fixture the piezoelectric crystal. To accomplish this without the use of specially formed vibrating surfaces as taught in the prior art, the revised contact structure of FIG. 5 was developed. While the upper contact 70 remains the same, the lower contact 72' is of greatly reduced diameter resulting in what is believed to be a vibrational wave pattern 74' which is wedge-shaped and centrally located, as depicted.

Figure 6:
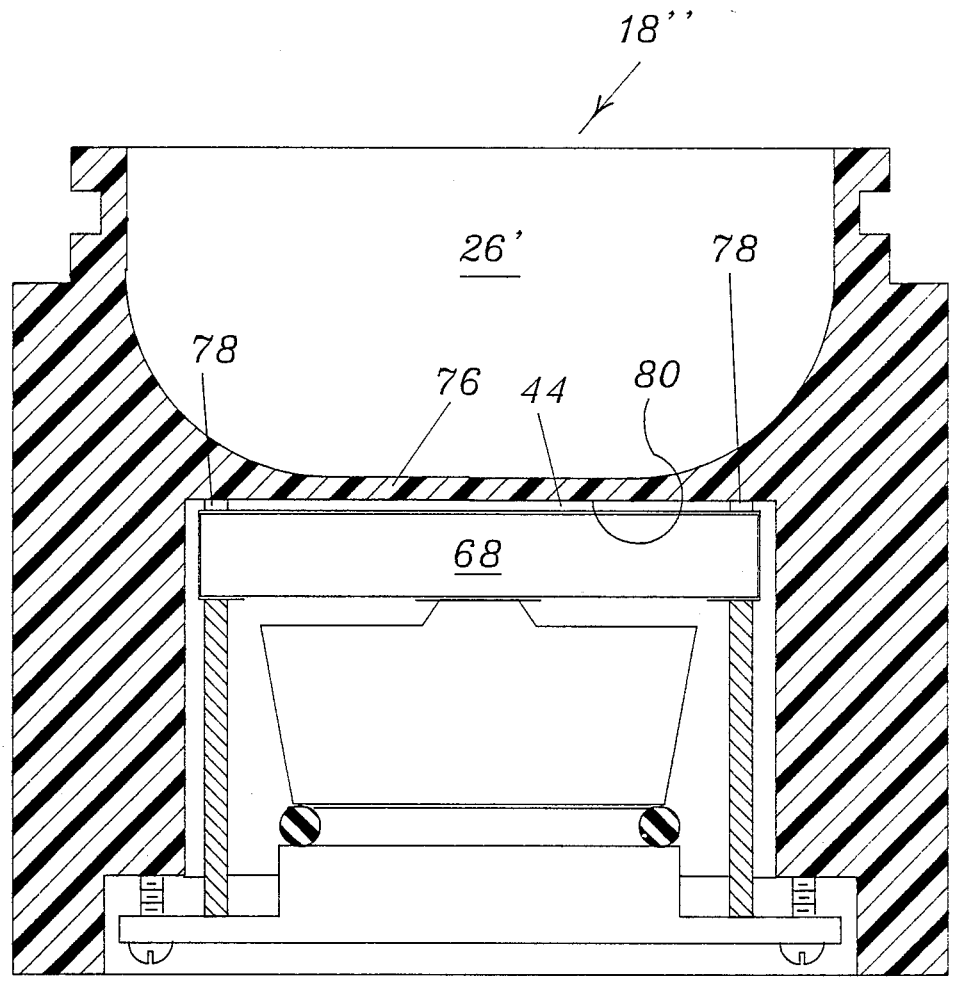
FIG. 6 is an enlarged, detailed, cutaway drawing of the bowl portion of a nebulizer according to the present invention in a second embodiment thereof.

Turning to FIG. 6 a nebulizer bowl portion according to a second embodiment of the present invention is indicated therein as 18''. For ease of comparison, like parts are described by like numbers. In the bowl portion 18'', the bowl 26' itself has no hole in the bottom as in the previously described embodiment. Rather, the bottom of the bowl 26' comprises a thin planar cover 76 of the same material as the rest of the bowl portion 18''. This makes the inside surface of the bowl 26' smooth and without cracks or joints. Such a design is sanitary and easy to clean. This embodiment would lend itself particularly well to being formed of one of the modern ceramic materials or high temperature plastics developed from space technology. As can be seen from the drawing, the piezoelectric crystal 68 is closely spaced and coupled directly to the planar cover 76 by the coupling fluid 44. A peripheral seal 78, such as, an O-ring, adhesive, or the like is disposed between the crystal 68 and the bottom 80 of the planar cover 76 to prevent the loss of the fluid 44, as previously described.

Figure 7:
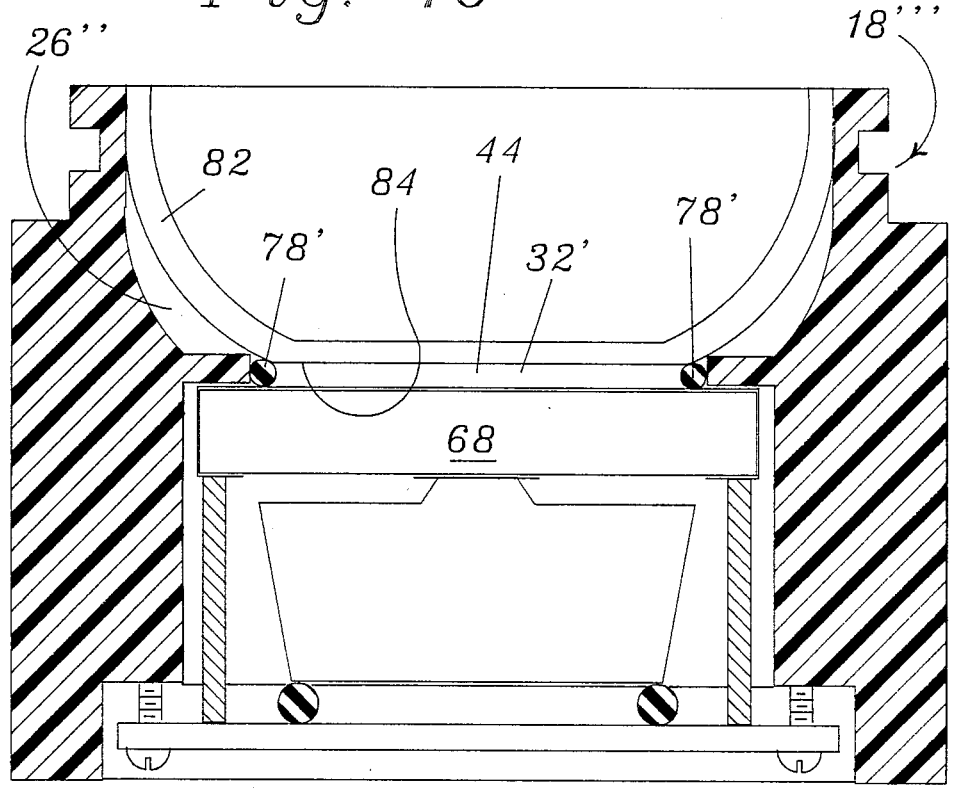
FIG. 7 is an enlarged, detailed, cutaway drawing of the bowl portion of a nebulizer according to the present invention in a third embodiment thereof.

Turning now to FIG. 7 a nebulizer bowl portion according to a third embodiment of the present invention is indicated therein as 18'''. For ease of comparison, like parts are again designated by like numbers. In the bowl portion 18''', the bowl 26' itself has hole 32' in the bottom as in the previously described embodiment of FIG. 3. To provide an inside surface for receipt of the medication which is smooth and without cracks or joints as in the second embodiment, a unitary bowl insert 82 is disposed within the bowl 26'' and over the hole 32'. The bowl insert can be of pyrex glass, plastic, ceramic, or the like, as desired. This design too is sanitary and easy to clean. As can be seen from the drawing, the piezoelectric crystal 68 is closely spaced and coupled directly to the bottom 84 of the bowl insert 82 by the coupling fluid 44. A peripheral seal 78', such as, an O-ring, adhesive or the like is disposed between the crystal 68 and the bottom 84 of the bowl insert 82 to prevent the loss of the fluid 44, as previously described.

A novel and improved form of portable nebulizer unit is illustrated in FIGS. 11 to 14 and comprises a generally cylindrical housing 120 which is divided into an upper chamber area 121 and a lower bowl section 122. The lower bowl section 122 defines a cavity 123 with a hole 124 in the bottom of the cavity directly above a piezoelectric crystal 126. The crystal 126 is covered by a one-half wave glass cover plate 127, the plate 127 being resiliently urged against an upper surface of the crystal by an elastomeric boot 128. As best seen from FIG. 12, boot 128 has an outer wall 130 which encircles the perimeter of the crystal 126 and plate 127 with a reservoir 129 in communication with the external edge of interface 125 between the crystal 126 and cover plate 127. The boot 128 has upper and lower annular return flanges 131 and 132, respectively, and is dimensioned such that it must be stretched over the crystal 126 and cover plate 127 so that the crystal 126 and cover plate 127 are pressed together in close-fitting sealed relation to the boot 128 without the necessity of an adhesive. An energy coupling oil film 133 is placed in the interface or gap 125.

A conventional thermoswitch 134 is supported beneath the crystal 126 by an annular plastic support member 136, and a cable retainer has a power pack connection 139 for a power pack unit, not shown.

A leaf spring contact 142 is interposed between the center or positive electrode 143 on the undersurface of the crystal 126 and is connected to a positive electrical strap 144 extending downwardly into the power pack connection 139. In turn, a negative electrical strap or lead 145 establishes contact with the outer, negative electrode 146 of the crystal and extends into the power pack connection 138.

The upper chamber area 121 is made up of inner and outer concentric tubes 150 and 151, respectively, which are arranged coaxially and in direct communication with respect to the bowl unit 122. The inner concentric tube 150 terminates at its upper end in an enlarged annular seat portion 152 which receives an on-off valve assembly 154, the valve assembly provided with flap valve members 156. The valve member 156 is a thin resilient membrane of generally circular configuration which is secured to a fixed hub 158 and radiates outwardly across openings 160. The valve membrane is normally biased in a direction closing the valve but when a negative pressure is created in the interior of the tube 150 it will cause the circular membrane to open and admit outside air in the direction of the arrows through the inner tube 150. The necessary negative pressure or suction is created by means of a mouthpiece 162 in communication with the concentric space 163 between the tubes 150 and 151 so as to cause air to be drawn downwardly through the tube and into the cavity of the bowl unit 122 so as to pick up particles of liquid medication generated by the piezoelectric crystal and which particles tend to erupt into a somewhat conical-shaped turbulent fountain within the cavity area formed by the bowl unit. The particles are entrained in the airstream and flow upwardly along a spiral flow path created by a spirally extending baffle 164 on the external surface of the inner tube 150 beneath the mouthpiece 162.

In devising a functional nebulizer it is important to match emitted particle size distribution to that required physiologically for effective respiratory treatment. Ultrasonic nebulizers typically produce a range of particle sizes, a significant number of which are larger than those clinically useful. These larger particles do not reach the respiratory tissues targeted for treatment and therefore represented wasted medication. In order to prevent particles larger than approximately 4 microns from exiting through the mouthpiece and going to the patient, the upper section of the nebulizer is provided with a particle impaction baffle 164 as described. The baffle will accelerate the particles through a circular path on their way to the mouthpiece and only the larger particles will tend to accumulate on the sidewalls and flow back downwardly into the bowl unit to be renebulized. As a result, essentially all liquid medication is converted to a mist of clinically useful particles to insure accurate and economical treatment.

Having considered the overall construction and arrangement of the form of nebulizer illustrated in FIGS. 11 to 14, a better understanding can be gained of the detailed construction and arrangement of the piezoelectric crystal 126 and its cover plate 127. As hereinbefore described, the crystal 126 has a center electrode 143 and outer spaced concentric negative electrode 146 surrounding the top surface and outer perimeter of the crystal. Preferably, the electrodes are composed of a thin coating or plating, such as, nickel, silver or gold. It is important that the coating selected be such that it will not tend to separate from the surface of the crystal and cause acoustic energy coupling losses and resultant reduction in nebulization. The cover plate 127 is preferably a glass material having a thickness of one-half wave length or a multiple thereof, such as, W, 3W/2, 2W and which is assembled to the transducer or crystal surface. Again, glass is a convenient material for such a cover since it presents an easily cleaned and durable surface to the liquid and can tolerate high temperatures. The liquid coupling film 133 serves to bridge the gap formed between the two confronting surfaces of the crystal 126 and cover plate 127. Preferably, the gap formed is a generally circular recess defined by a planar surface 126' and concave surface 127' on the crystal 126 and cover plate 127, respectively. This imposes a certain optimum oil film thickness while permitting the oil to migrate toward the high energy density center of the crystal glass interface; and further, the gap or recess avoids problems associated with a uniform recess depth which were found to lead to destruction of the transducer surface caused by concentric standing wave activity in the oil layer. The success of the oil coupling system suggests that the oil be contained so that gravity and capillary forces do not carry the coupling oil out of the gap during periods of inactivity. Nevertheless, the reservoir 129 formed in the boot permits storage of excess oil at the periphery of the gap and allows migration of the oil 133 toward the center when energy is applied to the transducer. Thus, the oil reservoir 129 permits the oil to expand with increased temperature rather than to separate the transducer from the glass. In addition, the boot 128 reduces damping by acoustically isolating the vibrating transducer and glass assembly from the outer housing.

Another problem associated with piezoelectric crystals in ultrasonic nebulizers is the tendency on the part of the porous surface of the crystal to hold entrapped gas which, when released during operation, can displace the oil and uncouple the glass cover so as to retard nebulization. In order to control this degenerative effect, it was found that a preassembly oil saturation treatment is extremely helpful and is carried out by placing the crystals in an oil bath surrounded by a very low pressure environment. The peripheral oil reservoir 129 in the boot 128 serves to accumulate any remaining entrapped gas which may escape from the transducer or crystal surface during its life. Accordingly, selective design of the piezoelectric assembly in the manner described has been found to result in superior energy transmission efficiency, increased power level tolerance while expanding the thermal range of the crystal to a point that a coolant is not required.

It is therefore to be understood that various modifications and changes may be made in the construction and arrangement of elements comprising preferred and alternate forms of apparatus as well as the particular sequence of steps described in connection with the method without departing from the spirit and scope thereof as defined by the appended claims.

We claim:

1. In an apparatus for the nebulization of fluids in which a piezoelectric transducer is disposed in communication with a fluid reservoir for nebulizing liquid medication in the fluid reservoir, the improvement comprising:

a protective cover member of a predetermined wavelength superimposed on said piezoelectric transducer, adjacent said reservoir said cover member and transducer having generally planar confronting surfaces and a common interface therebetween;

annular sealing means in outer surrounding relation to said cover member for preventing the loss of fluid from said interface; and oil coupling means in said interface for coupling the energy from said transducer to said cover member.

2. In apparatus according to claim 1, said cover member being in the form of a glass cover plate.

3. In apparatus according to claim 2, said interface between said confronting surfaces of said transducer and said cover plate including a gap tapering radially and outwardly from a central portion of said interface.

4. In apparatus according to claim 3, one of said confronting surfaces being of generally concave configuration and the other of said confronting surfaces being generally planar.

5. In apparatus according to claim 1, said annular sealing means being defined by an elastomeric boot resiliently urging said cover member and said transducer together, said boot provided with an oil reservoir in surrounding relation to said interface.

6. In apparatus according to claim 5, said elastomeric boot having an outer wall surrounding the outer periphery of said cover member and said transducer, said annular sealing means acting as a pressure limiting diaphragm whereby the pressure created by thermal expansion of said oil coupling means does not alter the interface between said cover member and said transducer.

7. In apparatus according to claim 1, including an air inlet portion in communication with said fluid reservoir, an outlet, means for inducing the flow of air into said fluid reservoir via said air inlet portion whereby to pick up nebulized liquid in particle form from said reservoir and direct mixed air and particles to said outlet, and baffle means in the path of flow of the mixed air and particles from said fluid reservoir toward said outlet to prevent larger sized particles from passing through said outlet.

8. In apparatus according to claim 7, wherein said baffle means is in the form of a generally spirally extending baffle member in the path of flow of mixed air and particles from said fluid reservoir toward said outlet.

9. In apparatus according to claim 7, said air inlet portion is defined by a generally tubular portion coaxially aligned with said fluid reservoir, and said baffle means including a spirally extending baffle member on an external surface of said tubular portion.

10. In apparatus according to claim 9, said outlet including an outer cylindrical portion in outer spaced concentric relation to said tubular portion and a mouthpiece in communication with the concentric space between said tubular portion and said outer cylindrical portion, said baffle means causing said larger particles to drain by gravity back into said fluid reservoir for renebulization.

* * * * *